(12) United States Patent
Obae et al.

(10) Patent No.: US 7,795,240 B1
(45) Date of Patent: Sep. 14, 2010

(54) NONREDUCING BETA-GLUCAN DERIVATIVE

(75) Inventors: Kazuhiro Obae, Nobeoka (JP); Ichiro Ibuki, Nobeoka (JP); Hirokazu Matsui, Sapporo (JP); Hiroyuki Ito, Sapporo (JP); Kenji Watanabe, Pasadena, CA (US)

(73) Assignee: Asahi Kasei Chemicals Corporation, Tokyo (JP)

( * ) Notice: Subject to any disclaimer, the term of this patent is extended or adjusted under 35 U.S.C. 154(b) by 1050 days.

(21) Appl. No.: 10/580,863

(22) PCT Filed: Nov. 26, 2004

(86) PCT No.: PCT/JP2004/017562

§ 371 (c)(1),
(2), (4) Date: May 26, 2006

(87) PCT Pub. No.: WO2005/052008

PCT Pub. Date: Jun. 9, 2005

(30) Foreign Application Priority Data

Nov. 28, 2003 (JP) .............................. 2003-398514

(51) Int. Cl.
*A61K 31/716* (2006.01)
(52) U.S. Cl. ...................................... 514/54
(58) Field of Classification Search .................... 514/54
See application file for complete search history.

(56) References Cited

U.S. PATENT DOCUMENTS

| 5,089,401 A | 2/1992 | Fujita et al. |
| 2003/0100749 A1 | 5/2003 | Withers et al. |

FOREIGN PATENT DOCUMENTS

| EP | 0 470 331 | | 2/1992 |
| EP | 0470331 | * | 12/1992 |
| JP | 60181102 | | 9/1985 |
| JP | 4091795 | | 3/1992 |
| JP | 8073506 | | 3/1996 |
| WO | WO 01/33973 | | 5/2001 |

OTHER PUBLICATIONS

Kobayashi et al, Int. J. Biol. Macromol. 1995, 17(6), 373-79.*
English abstract of Taiwanese Patent Publication No. 491689, published Jun. 21, 2002.
Taiwanese Patent Office Action, mailed Feb. 19, 2008 and issued in corresponding Taiwanese Patent Application No. 09720090560.
Shiro Kobayashi et al., "Chemical synthesis of cellulose and cello-oligomers using a hydrolysis enzyme as a catalyst", International Journal of Biological Macromolecules, Butterworth & Co., Guildford, Great Britain, vol. 17, No. 6, 1995, pp. 373-379.
K. Bhat et al., "Study of the mode of action and site specificity of the endo-(1-4)-beta-D-glucanases of the fungus *Penicillium pinophilum* with normal, $1-^3H$-labelled, reduced and chromogenic cello-oligosaccharides", Biochemical Journal, Portland Press, London, Great Britain, vol. 266, No. 2, Mar. 1, 1990, pp. 371-378.
Supplementary European Search Report, mailed Mar. 26, 2007, and issued in corresponding European Patent Application No. 04819431.0-2115.
Koki Fujita et al., "Transfer Reaction of β-Fructofuranosidase from *Anthrobacter* sp. K-I" Journal for starch and its related carbohydrates and enzymes, vol. 39, No. 2 pp. 135-142, 1992.
PCT International Search Report from Japanese Patent Office Mailed on Jan. 25, 2005.

* cited by examiner

*Primary Examiner*—Shaojia Anna Jiang
*Assistant Examiner*—Ganapathy Krishnan
(74) *Attorney, Agent, or Firm*—Staas & Halsey LLP

(57) ABSTRACT

A β-glucan derivative comprising a β-glucan residue of three or more glucose residues and, chemically bonded to the β-glucan residue, a non-reducing sugar residue.

12 Claims, 1 Drawing Sheet

NONREDUCING BETA-GLUCAN DERIVATIVE

This application is based on and hereby claims priority to PCT Application No. PCT/JP2004/017562 filed on Nov. 26, 2004 and Japanese Application No. 2003-398514 filed on Nov. 28, 2003, the contents of which are hereby incorporated by reference.

TECHNICAL FIELD

The present invention relates to a β-glucan derivative, a composition containing the β-glucan derivative and one or more active ingredients, and a process for producing the β-glucan derivative. More specifically, the present invention relates to a β-glucan derivative which rarely causes a chemical interaction (such as Maillard reaction) with an active ingredient having a terminal amino group and can be stably included in a composition in application such as medicines, agricultural chemicals, fertilizers, feed products, food products, industrial products and cosmetic products.

BACKGROUND ART

In solid preparations such as medicines, agricultural chemicals, fertilizers, feed products, food products, industrial products and cosmetic products, adding β-glucan powder such as micro crystalline cellulose and cellulose powder to an active ingredient to produce preparation can imparts binding property and disintegrability to the active ingredient. Such a preparation has advantages effects such that the shape of the preparation such as tablets and granules can be maintained, and that medical benefits of an active ingredient can be effectively produced since the preparation rapidly disintegrates in the digestive tract.

Of micro crystalline celluloses, one having excellent compactibility has the following advantages. Since it can be made into tablets at low compression pressure, the activity of an active ingredient, which tends to be inactivated by the compression pressure, can be maintained; film-coated granules-containing tablets can be formed; since it contributes to hardness of tablets in a small amount, a bulky active ingredient and a preparation containing various types of active ingredients can be made into tablets, in some cases, small-size tablets can be made; a support property of a liquid ingredient is superior; and damage caused by compression pressure can be suppressed.

However, a conventional micro crystalline cellulose and a cellulose powder had a problem. Since they have a highly reactive reducing group (carbonyl group) at a reducing end, the amino-carbonyl reaction (Maillard reaction) may take place between the reducing end and a terminal amino group of an active ingredient to produce an amino carbonyl bond and the bond causes color, and therefore, a micro crystalline cellulose and a cellulose powder cannot be added to a preparation using such an ingredient.

As a method for inactivating the reducing end of the micro crystalline cellulose and cellulose powder, the following methods may be mentioned:

(1) a method of using a reducing agent such as sodium borohydride to convert the reducing end into an alcohol;

(2) a method of using an oxidant such as sodium chlorite to convert the reducing end into carboxylic acid; and (3) a method of chemical modification of the reducing end by enzymatic treatment or the like.

However, the methods (1) and (2) have a problem of safety, that is a reducing agent or an oxidant remains in a micro crystalline cellulose and a cellulose powder finally obtained; and a problem of functional deterioration, that is depolymerization proceeds during the reaction, and it lowers moldability. In the method (3), when a sugar chain is added by transglucosylation mediated by a transferase or a hydrolase, in most cases, the transglucosylation proceeds from a non-reducing end. Therefore, it has been considered that it is impossible to enzymatically perform chemical modification of the reducing end of a micro crystalline cellulose and a cellulose powder.

On the other hand, with a recent increase of heath concern, synthesis etc. of oligosaccharides having various physiological activities and useful glycosides using a glycosyl transferase or fructosyl transferase have been aggressively studied. Consequently, saccharides such as coupling sugar, fructooligosaccharide, palatinose, and α-glycosylstebiocide have been put into practical use as a substance having properties as anti-dental caries and a Lactobacillus bifidus proliferation factor. A levan sucrase produced by Bacillus subtilis and a β-fructofuranosidase produced by a mold such as *Aspergillus niger, Penicllium oxalicum, Penicllium frequentans,* and *Penicillium* sp. K25 are known as a fructosyltransferase.

Patent Document 1 and Non-Patent Document 1 describe a transglucosylation mediated by β-fructofuranosidase produced by *Arthrobacter* sp. K-1 stain. However, as an example of β-glucan, they only describe that a product produced from cellobiose having two glucose residues as a substrate. These documents do not describe an usefulness of a product such that a fructose is bound to β-glucan having three or more glucose residues and a product wherein fructose is bound to the reducing end of a micro crystalline cellulose and a cellulose powder; more specifically, an usefulness such that they successfully make a preparation using an active ingredient (which has not yet been able to use) having an amino group, by inactivating the reaction with an active ingredient while maintaining its inherent natures such as moldability and disintegrability.

Patent Document 1: JP-A-4-91795

Non-Patent Document 1: Denpun Kagaku, Vol. 39, No. 2, p. 135-142 (1992)

DISCLOSURE OF THE INVENTION

Problems to be Solved by the Invention

The present invention is, in view of the aforementioned problems, to provide a cellulose powder, which does not cause a chemical interaction (such as Maillard reaction) with an active ingredient having a terminal amino group, can be stably contained in a composition and is free from a safety problem and functional deterioration, for applications such as medicines, agricultural chemicals, fertilizers, feed products, food products, industrial products and cosmetic products.

Means for Solving the Problems

The present inventors conducted extensive studies on transglucosylation to a cellulose. As a result, the inventors found that β-fructofrunosidase produced from the genus *Arthrobacter* could mediate effectively transglucosylation from a reducing end. This finding led to the completion of the present invention. More specifically, the present invention is described as follows:

(1) A β-glucan derivative having a β-glucan residue having three or more glucose residues and a non-reducing sugar residue chemically bound to the β-glucan residue.

(2) The β-glucan derivative according to (1) having 3 to 1000 glucose residues.

(3) The β-glucan derivative according to (1) or (2) having 3 to 450 glucose residues.

(4) The β-glucan derivative according to any one of (1) to (3) having 40 to 450 glucose residues.

(5) The β-glucan derivative according to any one of (1) to (3) having 3 to 39 glucose residues.

(6) The β-glucan derivative according to any one of (1) to (4) having 40 to 450 glucose residues, characterized in that the β-glucan derivative is used as an additive for pharmaceuticals and foods.

(7) The β-glucan derivative according to any one of (1) to (3) and (5) having 3 to 39 glucose residues, characterized in that the β-glucan derivative is used as an additive for pharmaceuticals and foods.

(8) The β-glucan derivative according to any one of (1) to (7), wherein the non-reducing sugar is a fructosyl group.

(9) The β-glucan derivative according to any one of (1) to (8), wherein the chemical bond between the β-glucan residue and the non-reducing sugar residue is an ether bond or an ester bond.

(10) The β-glucan derivative according to any one of (1) to (9), wherein the chemical bond between β-glucan residue and non-reducing sugar residue is an ether bond.

(11) The β-glucan derivative according to any one of (1) to (10), wherein the β-glucan derivative is powder at ordinary temperature and pressure.

(12) A β-glucan derivative having three or more glucose residues produced by chemically binding a non-reducing sugar to a reducing end.

(13) The β-glucan derivative according to (12) having 3 to 1000 glucose residues produced by chemically binding a non-reducing sugar to a reducing end.

(14) The β-glucan derivative according to (12) or (13) having 3 to 450 glucose residues produced by chemically binding a non-reducing sugar to a reducing end.

(15) The β-glucan derivative according to any one of (12) to (14) having 40 to 450 glucose residues produced by chemically binding a non-reducing sugar to a reducing end.

(16) The β-glucan derivative according to any one of (12) to (15) having 3 to 39 glucose residues produced by chemically binding a non-reducing sugar to a reducing end.

(17) The β-glucan derivative according to any one of (12) to (15) having 40 to 450 glucose residues produced by chemically binding a non-reducing sugar to a reducing end, characterized in that the β-glucan derivative is used as an additive for pharmaceuticals and foods.

(18) The β-glucan derivative according to any one of (12) to (14) and (16) having 3 to 39 glucose residues produced by chemically binding a non-reducing sugar to a reducing end, characterized in that the β-glucan derivative is used as an additive for pharmaceuticals and foods.

(19) The β-glucan derivative according to any one of (12) to (18), wherein the non-reducing sugar is a fructosyl group.

(20) The β-glucan derivative according to any one of (12) to (19), wherein the chemical bond between β-glucan residue and non-reducing sugar residue is an ether bond or an ester bond.

(21) The β-glucan derivative according to any one of (12) to (20), wherein the chemical bond between β-glucan residue and non-reducing sugar residue is an ether bond.

(22) The β-glucan derivative according to any one of (12) to (21), wherein the β-glucan derivative is powder at ordinary temperature and pressure.

(23) A pharmaceutical or food composition comprising the β-glucan derivative according to any one of (1) to (22) and at least one active ingredient.

(24) A process for producing the β-glucan derivative according to any one of (1) to (23) comprising providing the β-glucan according to any one of (1) to (23) and sucrose as substrates and allowing an enzyme to transglucosylate a fructosyl group in said sucrose to said β-glucan.

(25) The process for producing the β-glucan derivative according to any one of (1) to (24), wherein the enzyme for use in the transglucosylation is β-fructofuranosidase.

ADVANTAGES OF THE INVENTION

A β-glucan derivative of the present invention has an effect of providing compositions which are principally used in medicines and food products, rarely cause a chemical interaction (such as Maillard reaction) with an active ingredient having a terminal amino group and free from a problem of stability and functional deterioration as an additive for medicines and food products.

BEST MODE FOR CARRYING OUT THE INVENTION

Figure 1:
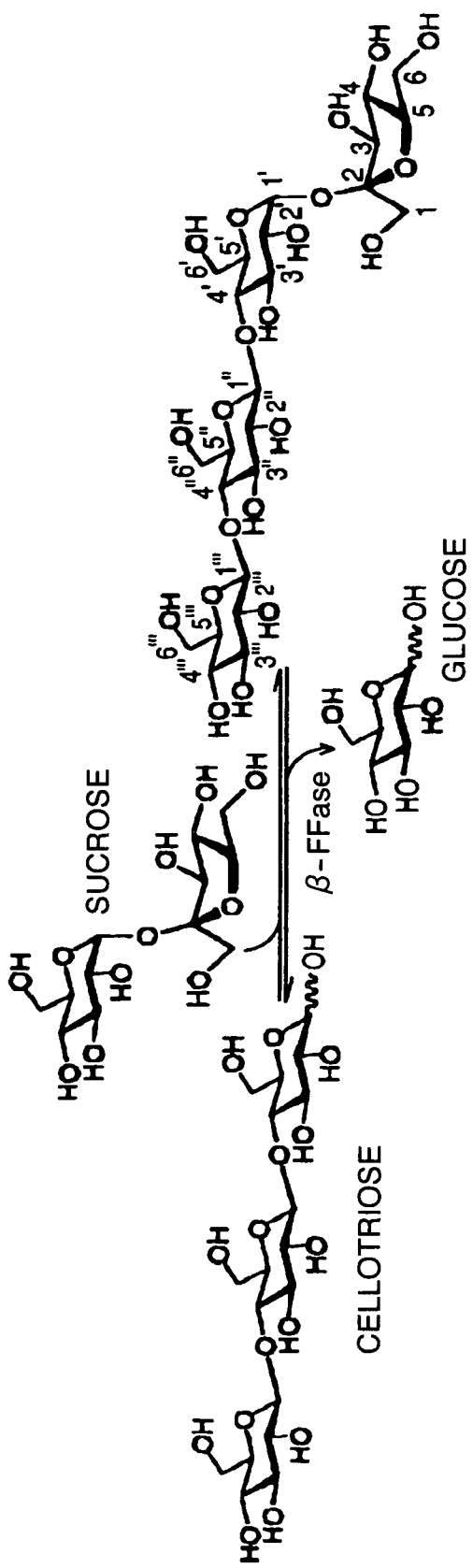
FIG. 1 schematically shows a transglucosylation reaction and a transglucosylated product.

The present invention are described in detail as mentioned below.

According to the present invention, β-glucan must have three or more glucose residues. The number of glucose residues herein refers to that of β-glucan serving as a substrate. When the number is less than 3, water-solubility becomes high. As a result, sufficient disintegration function cannot be imparted to a molded product containing the β-glucan according to the present invention. Furthermore, since powder grains have poor strength, a sufficient compactibility cannot be imparted to a molded product. The term "disintegrability" used herein refers to a function of disintegrating a molded product such as a tablet and a granule in water when the β-glucan derivative is used as an excipient and is responsible for water dispersibility and fast-acting property of an active ingredient of a medicine or the like. The term "compactibility" used herein refers to a function of imparting sufficient strength to a molded product when a composition or grains containing the β-glucan derivative as an excipient is molded under compression into a molded product such as a tablet. The upper limit of the number of glucose residues is not particularly specified. However, when the number of cellulose residues contained in a β-glucan derivative is too large, particles of the β-glucan derivative become fibrous, with the result that the compactibility and disintegrability decrease. Therefore, a rough indication of the number of glucose residues is up to 1000. To keep excellent balance between compactibility and disintegrability, the number of glucose residues is preferably 6 to 800, more preferably, 40 to 450.

When a β-glucan derivative according to the present invention is used as a physiologically active agent, the number of glucose residues is preferably 3 or more, more preferably 3 to 1000, further preferably 3 to 450, and most preferably 3 to 39. The "physiologically active" used herein refers to an activity derived from the chemical structure of a non-reducing β-glucan derivative according to the present invention and producing an advantageous effect upon a human body, and more specifically, it refers to a physiological activity derived from the chemical structure of β-glucan and/or a non-reducing sugar. To express the physiological activity, a β-glucan derivative preferably has a hydrophilicity to some extent. To acquire the above described hydrophilicity, the number of glucose residues is preferred to be within the aforementioned range. The physiological activity derived from a β-glucan structure may include an activity of activating flora of useful enterobacteria such as *Lactobacillus bifidus* and *lactobacillus*, activity of fermenting a short-chain/middle-chain fatty acid, activity of metabolizing a lipid and a saccharide and activity of improving bowl movement. Furthermore, the physiologically activity derived from the non-reducing sugar site (moiety), when a fructosyl group is contained as a non-reducing sugar group, may include an activity of improving allergy, activity of enhancing hepatic function, activity of enhancing immunity and activity of improving intestinal absorption of mineral.

In a β-glucan derivative according to the present invention, the glass transition point of the β-glucan moiety as a receptor of the non-reducing sugar is preferably 55° C. or more. The glass-transition point herein is measured by differential scanning colorimetry (DSC). The glass transition point is an indicator showing the crystallinity of a β-glucan and closely relates to the above described disintegrability of a molded product. The higher the glass transition point is, the lower the solubility of powder of a β-glucan derivative becomes. As a result, the disintegrability of the molded product increases. When the glass transition point is less than 55° C., the disintegrability of a molded product decreases since the solubility of a β-glucan derivative increases. The glass transition point is particularly preferably 60° C. or more, and further preferably 70° C. or more.

In a β-glucan derivative according to the present invention, a non-reducing end needs not to be bound to all reducing ends. A non-reducing end may be bound to reducing ends to the extent that an active ingredient such as a medicament or the like having an amino group is stably present. The conversion rate of a reducing end of the β-glucan into a non-reducing end is preferably 0.1 mol % or more. Whether an active ingredient is present in a stable state can be readily checked by an observation based on degree of coloration in a storage stability test in a condition that is performed by mixing an active ingredient and a β-glucan derivative in equivalent amounts and stored the mixture at 40° C. under 75%. Since it has a reducing end, β-glucan is known to initiate the Maillard reaction with an active ingredient having a terminal amino group to form an amino-carbonyl bond and produce color. However, a β-glucan derivative according to the present invention has an advantageous effect in that since the reducing end is inactivated by a non-reducing sugar, no coloring reaction takes place. The effect of the present invention is particularly effective for an active ingredient having a primary amine.

A process for producing a β-glucan according to the present invention is not particularly limited as long as the reducing end of the chemical structure of the β-glucan can be converted into a non-reducing end. For example, it is preferable to employ a process for binding chemically a non-reducing sugar to a reducing end of the β-glucan. The non-reducing sugar used herein refers to a sugar residue to be bound to a C-1 position of the reducing end of the β-glucan. A type, a structure, a binding site to β-glucan and a linkage configuration such as α-linkage or β-linkage of the non-reducing sugar are not particularly limited as long as the β-glucan derivative becomes non-reducing type when the reducing sugar binds to the C-1 position of the β-glucan to be a β-glucan derivative.

Examples of such a non-reducing sugar bound to the β-glucan includes monosaccharides including known hexoses such as fructose, glucose, galactose and mannose, isomers and derivatives thereof; pentoses such as xylose and arabinose, isomers and derivatives thereof; and tetroses such as erythrose and threose, isomers and derivatives thereof. Among them, when fructose is employed as a non-reducing sugar, a fructose residue is transferred from sucrose to a reducing end of β-glucan and the C-2 position of the fructose is bound to the C-1 position of the reducing end of β-glucan to make the terminal of the β-glucan derivative a sucrose structure. The obtained β-glucan derivative is non-reductive. In contrast, since the C-1 position of glucose, galactose and mannose is reductive, it is necessary to bind the reducing end (the C-1 position) of the β-glucan to the C-1 position of a sugar residue of the same. Furthermore, as an example of a disaccharide serving as a non-reducing sugar to be bound to the reducing end (the C-1 position) of the β-glucan according to the present invention, include disaccharides such as sucrose and trehalose, which themselves are not reductive, isomers and derivatives thereof. Other than the above described sucrose and trehalose, disaccharides obtained from known sugars such as hexoses, pentose, and tetrose in combination by binding the C-1 positions of the constituents monosaccharides, may be used as long as the resultant sugar is non-reductive. Since such the non-reducing disaccharides are nonreductive, they may be bound to any component monosaccharides as long as they binds to the C-1 position of the β-glucan. Among them, a non-reducing sugar obtained by binding the C-2 position of fructose to the C-1 position of the reducing end of β-glucan by enzymatic transglucosylation is preferable, as non-reducing sugar to be bound to the reducing end of the β-glucan, in view of yield.

Any β-glucan derivatives may be used in the present invention as long as a non-reducing sugar is bound to β-glucan having three or more glucose residues by known chemical synthesis reactions or known enzyme reactions. However, from a safety point of view and functional point of view, the method using a fructose transfer reaction mediated by β-fructofuranosidase is most effective. To bind fructose, known chemical synthesis reactions and known enzyme reactions may be used. Known starting materials for such reactions may also be used.

The β-fructofuranosidase used in the present invention is microbially produced. Any producing microbes may be used for producing β-fructofuranosidase, if it belongs to the genus *Arthrobacter* and is capable of producing an enzyme mediating fructose transfer reaction. For example, *Arthrobacter globiformis* NBRC 3062, *Arthrobacter aurescens* or the like, mutant species and mutant strains thereof etc. are included. Arthrobacter globiformis NBRC 3062 was previously available from the Institute for Fermentation under Strain No. IFO 3062. However, since Jul. 1, 2002, it is available from the National Institute of Technology and Evaluation (Independent Administrative Institution), Department of Biotechnology, Biological Resource Center (NBRC) under Strain No. NBRC 3062. Note that the strain used herein was also deposited by the applicant under the name of *Arthrobacter globiformis* (Conn 1928) Conn and Dimmick 1947, on Nov. 5, 2004 at Independent Administrative Institution, the International Patent Organism Depositary of the National Institute of Advanced Industrial Science Technology (located at Tsukuba Central 6, 1-1-1 Higashi, Tsukuba, Ibaraki, Japan, postal code: 305-8566) and under deposition No. FERM BP-10159 under the Budapest Treaty on the International Recognition of the Deposit of Microorganisms for the Purposes of Patent Procedure. As a means for mutagenesis, a known method may be used including radioisotope, UV rays, nitrosoguanidine and gene recombination.

A medium for culturing the aforementioned microorganism is not particularly limited and any medium may be used as long as it has a composition containing a carbon source and a nitrogen source and it makes microbes most efficiently produce microbially producing β-fructofuranosidase. Examples of the carbon source include sucrose, maltose, lactose and soluble starch or the like. Examples of the nitrogen source include nitrate, ammonium salt, yeast extract, corn steep liquor or the like. Other than these, inorganic salts such as magnesium salt, calcium salt, and phosphate or the like and nutritive substances required for microbial growth may be appropriately added to a medium. A composition of a preferable medium may include, for example, 1% polypeptone, 0.2% yeast extract, 0.1% MgSO$_4$.

To produce β-fructofuranosidase used in the present invention, the aforementioned microbe is inoculated and cultured at pH in the range of neutral to weak acid for about 10 hours to several days with shaking or agitating under aeration, with maintaining a temperature of 20° C. to 45° C., preferably 30° C. to 40° C. The enzyme can be collected and purified from thus obtained cultures by a known method. For example, the supernatant obtained from the cultures which is subjected to centrifugation to remove microbes can be used as a crude enzyme solution. If necessary, further purification can be made, for example, by a salting-out method, hydrophobic chromatography, gel filtration, and ion-exchange chromatography or combination thereof.

The β-fructofuranosidase used in the present invention is enzymatically induced type by sucrose and exhibits its optimal activity at a concentration of about 2.5% which is optimal concentration for sucrose.

A β-glucan derivative according to the present invention can be obtained by the following method, but not limited thereto, which includes, for example, reacting the β-fructofuranosidase obtained as described above with sucrose in the presence of β-glucan having three or more glucose residues to obtain a dispersion solution containing a β-glucan derivative wherein a fructose as non-reducing sugar is bound to its terminal, followed by subjecting to dehydration. In performing the reaction, the reaction conditions should be selected in consideration of the nature of the enzyme such that a β-glucan derivative having a fructose as a non-reducing sugar at a desired end can be purified in the largest amount. The dehydration method is not particularly limited. Examples thereof include a general dehydration methods such as lyophilization, spray drying, drum drying, plate drying, air drying, vacuum drying and dehydration with an organic solvent.

The β-fructofuranosidase used in the present invention is preferably a single purified enzyme having a molecular weight of 60000, a specific activity of 102 U/mg, a reaction rate parameter of Km=2.6 mM and Vmax=127 μmol/min/mg.

As an example of a enzyme having exactly the same fructose transfer activity as that of β-fructofuranosidase, it may include a protein cloned from a gene encoding β-fructofuranosidase which is isolated from the above described Arthrobacter globiformis NERC 3062 (FERM Deposition No. FERM BP-10159). While it is impossible to describe all information as to this protein, N-terminal structure analysis revealed that the protein has a specific sequence consisting of 10 amino acids represented by ATDAAPGFPQ (SEQ ID. No. 1) where A: alanine, T: threonine, D: aspartic acid, P: proline, G: glycine, F: phenylalanine, and Q: glutamine. Therefore, it can be confirmed by checking the sequence consisting of 10 amino acids in the N-terminal of a protein contained in the reaction system whether the used enzyme has the fructose transfer activity of the present invention.

The β-glucan derivative of the present invention may be a composition containing the β-glucan derivative of the present invention and one or more active ingredients. The active ingredient refers to a pharmaceutically active ingredient, agricultural chemical ingredient, fertilizer ingredient, feed ingredient, food product ingredient, cosmetic ingredient, dye, flavor, metal, ceramic, catalyst surfactant or the like. The active ingredient may take any form such as a powder, crystalline, oily, liquid, or semisolid form, and also may be fine powder and granules. Furthermore, the active ingredient may be coated in order to control dissolution and mask bitter taste. The active ingredient may be used independently or in a combination of two or more of the same.

Examples of the pharmaceutically active ingredient include oral drugs such as antipyretic analgesic, sedative hypnotic, drowsiness preventing drug, anti-vertiginous drug, analgesics for child, stomachic, antacid, digestive agent, cardiotonic drug, arrhythmia drug, antihypertensive drug, vasodepressor, diuretic drug, antiulcer drug, drug for controlling intestinal function, osteoporosis therapeutic drug, antitussive agent, antiasthmatic drug, antibiotics, frequent urination improver, analeptic, and vitamins. The active ingredient may be used independently or in a combination of two or more of the same.

The composition used herein may contain, other than an active ingredient and a β-glucan derivative according to the present invention, ingredients such as an excipient, disintegrator, binder, fluidization agent, lubricant, flavoring agent, flavor, colorant and sweetener, as needed. Furthermore, these ingredients may be used as a diluent.

Examples of the binder include saccharides such as white sugar, glucose, lactose, fructose, and trehalose; sugar alcohols such as mannitol, xylitol, maltitol, erythritol, and sorbitol; water soluble polysaccharides such as gelatin, pullulan, carageenan, locust bean gum, agar, gluconan, xanthan gum, tamarind gum, pectin, sodium alginate, and gum arabic; celluloses such as micro crystalline cellulose (for example, Ceolus PH-101, PH-101D, PH-101L, PH-102, PH-301, PH-301Z, PH-302, PH-F20, PH-M06, M15, M25, and Ceolus KG-801 and KG-802, etc. manufactured by Asahi Kasei Chemicals Corporation), powdered cellulose, hydroxypropylcellulose, and methylcellulose; starches such as pregelatinized and starch paste; synthetic polymers such as polyvinyl pyrrolidone, carboxyvinyl polymer, and polyvinyl alcohol; and inorganic compounds such as phosphate hydrogen calcium, calcium carbonate, synthetic hydrotalcite, magnesium silicoaluminate. These may be used independently or in a combination of two or more of the same.

Of the micro crystalline celluloses, cellulose which is excellent in compactibility has the following advantages: the activity of an active ingredient which is inactivated by compression pressure can be maintained since tablets can be made at a low compression pressure, a film-coated granules-containing tablets can be made; bulky active ingredient and a drug containing a plurality of active ingredients can be made into tablets since hardness can be imparted by adding cellulose in a small amount, and, in some cases, tablets can be miniaturized; support property of a liquid component is excellent; and damage caused by tableting can be suppressed.

Examples of the disintegrator include celluloses such as sodium croscarmellose, carmellose, calcium carmellose, sodium carmellose, and low-substituted hydroxypropyl cellulose; starches such as sodium carboxymethyl starch, hydroxypropyl starch, rice starch, wheat starch, corn starch, potato starch, and partially pregelatinized starch; celluloses such as micro crystalline cellulose and powdered cellulose; and synthetic polymers such as crospovidone and crospovidone copolymer. These may be used independently or in combination of two or more of the same.

Examples of the fluidizing agent include silicon compounds such as water-containing silicon dioxide and light anhydrous silicic acid. These may be used independently or in combination of two or more of the same.

Examples of the lubricant agent include magnesium stearate, calcium stearate, stearic acid, sucrose fatty acid ester and talc. These may be used independently or in combination of two or more of the same.

Examples of the flavoring agent include glutamic acid, fumaric acid, succinic acid, citric acid, sodium citrate, tartaric acid, malic acid, ascorbic acid, sodium chloride and 1-menthol. These may be used independently or in combination of two or more of the same.

Examples of the flavoring include oils such as orange, vanilla, strawberry, yogurt, menthol, fennel oil, cassia oil, spruce oil and peppermint oil; and green tea powder. These may be used independently or in combination of two or more of the same.

Examples of the colorants include food colorants such as food color red No. 3, food color yellow No. 5, and food color blue No. 1, sodium copperchlorophyllin, titanium oxide, and riboflavin. These may be used independently or in combination of two or more of the same.

Examples of the sweetener include aspartame, saccharin, dipotassium glycyrrhizinate, stevia, maltose, maltitol, glutinous starch syrup and hydrangea powder. These may be used independently or in combination of two or more of the same.

Examples of the composition used for medicines include solid preparations such as tablets, powders, fine granules, granules, extracts, pills, and dry syrup. They can be prepared by a known method such as piston granulation, pulverization granulation, fluidized bed granulation, high-speed stirring granulation and rolling motion fluidized bed granulation. Furthermore, a liquid agent such as a drink can be prepared by a known method. Use of the composition according to the present invention is not limited to a medicine but for food such as confectionary, health food, texture improvers, and food fiber supplement, solid foundation, bath agents, animal drugs, diagnostic agents, agricultural chemicals, fertilizers and ceramic catalysts.

The composition used herein is preferably made into tablets in view of productivity, administration property, and easiness of handling. Such a tablet can be obtained by a direct compression tableting method, dry grain compression method, wet grain compression method and a tableting method comprising adding a disintegrator. Alternatively, the composition may be made into multi-core tablets using a tablet previously prepared by compression molding as an inner core. However, in view of cost and convenience, tablets formed by the direct compression tableting method are particularly preferable.

A composition according to the present invention may be coated with a coating material for the purpose of masking taste and moisture prevention. Examples of such a coating material include cellulose based coating materials such as ethyl cellulose, hydroxypropylmethyl cellulose phthalate, carboxylmethylethyl cellulose, hydroxypropylmethyl cellulose acetate succinate, cellulose acetate succinate, cellulose acetate phthalate and cellulose acetate; acrylic polymers based coating materials such as EUDRAGIT RS, EUDRAGIT L and EUDRAGIT NE; shellac; and a silicon resin. These may be used independently or in a combination of two or more of the same. These coating materials may be used in accordance with a known method. More specifically, such a coating material may be dissolved in an organic solvent or suspended in water. It is at liberty to make a coating material suspended in water into tablets together with a pharmaceutically active ingredient and other ingredients.

The β-glucan derivative powder of the present invention is expected to work as a factor of increasing beneficial enterobacteria such as Lactobacillus bifidus and as a food fiber for controlling intestinal function in medicines and food products. It is at liberty to add the β-glucan derivative powder to a composition for these purposes.

The present invention will be described in detail below by way of Examples, which will not be construed as limiting the present invention.

Production Example 1

To a general agar slant medium, Arthrobacter globiformis NBRC 3062 (FERM deposition No. BP-10159) was inoculated, cultured at 37° C. for 2 days. Thereafter; an aliquot was taken from the cultured product by a platinum loop, inoculated in a medium consisting of a composition of 1% of poly peptone, 0.2% of yeast extract, and 0.1% of $MgSO_4$, and incubated at 30° C. for 2 days while shaking under aeration. The culture solution was centrifuged, and the supernatant was subjected to DEAE-toyopearl 650M chromatography, further the eluate was subjected to Toyopearl HW-55 gel-filtration and then FPLC chromatography to obtain a purified enzyme.

Example 1

To 5% of sucrose and 5% of cellotriose (manufactured by Aldrich), the purified enzyme produced in Production Example 1 was added. The solution was allowed to react in a phosphate buffer (pH 7.0), at 37° C. for 20 hours to obtain a transglucosylated cellotriose wherein fructose is binding to the reducing end thereof. The structure of transglucosylated cellotriose was confirmed by proton NMR and carbon NMR (FIG. 1 and Table 1).

Whether fructose was bound was confirmed based on an increase of a peak [180-18] in a mass spectrum and a storage stability test of an equivalent mixture of the obtained transglucosylated product and L-arginine contained at 40° C. and 75% RH, airtight for 2 weeks. A decrease ratio in degree of whiteness was 2% (it was 99% at the onset and 97% after the test). White color in appearance was maintained.

Two mg of the transglucosylated product thus obtained was introduced in a cylindrical mortar of φ8 mm, and compressed by a flat-surface punch of φ8 mm at 25 kN for 10 seconds to obtain a molded cylindrical product.

The hardness of the molded cylindrical product thus obtained was measured by a Schleuniger hardness tester type 6D (Trademark, manufactured by FREUND Corporation). More specifically, a load pressure was applied to the molded cylindrical product or a tablet in the direction of the diameter to break it. The weight at the moment was measured. The hardness was represented by an average value of 10 samples. Furthermore, the disintegration time of the molded cylindrical product was determined in accordance with a general test method, a disintegration test method for tablets specified in the Japanese Pharmacopeia, 14th revision, by use of a disintegration tester (Toyama Sangyo Co., Ltd., Trade name: NT-40HS type with a disk), at 37° C. in pure water. The disintegration time was represented by an average of 6 tablets The hardness of the molded cylindrical product was 70 N and the disintegration time was 58 seconds.

Example 2

To 1.25% of sucrose and 1.25% of β-glucan having 40 glucose residues, the purified enzyme obtained in Production Example 1 was added. The mixture was allowed to react in a phosphate buffer (pH 7.0) at 37° C. for 9 hours to obtain a transglucosylated product wherein fructose is binding to the reducing end of the β-glucan having 40 glucose residues.

Whether fructose was bound was confirmed based on an increase of a peak [180-18] in a mass spectrum and a storage stability test performed by an equivalent mixture of the obtained transglucosylated product and L-arginine contained at 40° C. and 75% RH, airtight for 2 weeks. A decrease ratio in degree of whiteness was 3% (it was 99% at the onset and 96% after the test). White color in appearance was maintained.

A molded cylindrical product was prepared at a compression pressure of 1 kN in the same manner as in Example 1 and the hardness and disintegration time were determined. As a result, the hardness and the disintegration time of the molded cylindrical product were 60 N and 40 seconds, respectively.

Example 3

To 1.25% of sucrose and 1.25% of β-glucan having 220 glucose residues, the purified enzyme obtained in Production Example 1 was added. The obtained mixture was allowed to react in a phosphate buffer (pH 7.0) at 37° C. for 9 hours to obtain a transglucosylated product having fructose bound to the reducing end of the β-glucan having 220 glucose residues.

Whether fructose was bound was confirmed based on an increase of a peak [180-18] in a mass spectrum and a storage stability test performed by an equivalent mixture of the obtained transglucosylated product and L-arginine contained at 40° C. and 75% RH, airtight for 2 weeks. A decrease ratio in degree of whiteness was 2% (it was 99% at the initiation time and 97% after the test). White color in appearance was maintained.

A molded cylindrical product was prepared at a compression pressure of 0.75 kN in the same manner as in Example 1 and the hardness and disintegration time were measured. As a result, the hardness and the disintegration time of the molded cylindrical product were 60 N and 26 seconds, respectively.

Example 4

To 1.25% of sucrose and 1.25% of β-glucan having 500 glucose residues, the purified enzyme obtained in Production Example 1 was added. The mixture was allowed to react in a phosphate buffer (pH 7.0) at 37° C. for 9 hours to obtain a transglucosylated product having fructose bound to the reducing end of the β-glucan fructose having 500 glucose residues.

Whether fructose was bound or not was confirmed by determining degree of polymerization and a storage stability test performed by an equivalent mixture of the obtained transglucosylated product and L-arginine contained at 40° C. and 75% RH, airtight for 2 weeks. A decrease ratio in degree of whiteness was 1% (it was 99% at the onset time and 98% after the test). White color in appearance was maintained.

A molded cylindrical product was prepared at a compression pressure of 0.5 kN in the same manner as in Example 1 and the hardness and disintegration time were measured. As a result, the hardness and the disintegration time of the molded cylindrical product were 80 N and 280 seconds, respectively.

Comparative Example 1

An equivalent mixture of Ceolus PH-101, β-glucan having 220 glucose residues (manufactured by Asahi Kasei Chemicals Corporation) and L-arginine contained was subjected to a storage stability test (40° C., 75% RH, airtight, 2 weeks). As a result, a decrease ratio in degree of whiteness was 10% (it was 99% at the initiation time and 89% after the test). The mixture was apparently changed yellow.

Comparative Example 2

To 5% of sucrose and 5% of cellobiose (manufactured by Aldrich), the purified enzyme produced in Production Example 1 was added. The mixture was allowed to react in a phosphate buffer (pH 7.0) at 37° C. for 20 hours to obtain a transglucosylated cellobiose having fructose bound to the reducing end thereof.

Whether fructose was bound was confirmed by determining degree of polymerization and a storage stability test performed by an equivalent mixture of the obtained transglucosylated product and L-arginine at 40° C. and 75% RH, airtight for 2 weeks. A decrease ratio in degree of whiteness was 3% (it was 99% at the initiation time and 96% after the test). White color in appearance was maintained.

A molded cylindrical product was prepared at a compression pressure of 35 kN in the same manner as in Example 1 and the hardness and disintegration time were measured. As a result, the hardness and the disintegration time of the molded cylindrical product were 80 N and 300 seconds, respectively.

Reference Example 1

To 1.25% of sucrose and 1.25% of β-glucan having 1064 glucose residues, the purified enzyme obtained in Production Example 1 was added. The mixture was allowed to react in a phosphate buffer (pH 7.0) at 37° C. for 12 hours to obtain a transglucosylated product having fructose bound to the reducing end of the β-glucan having 1064 residues.

Whether fructose was bound was confirmed by determining degree of polymerization and a storage stability test performed by an equivalent mixture of the obtained transglucosylated product and L-arginine contained at 40° C. and 75% RH, airtight for 2 weeks. A decrease ratio in degree of whiteness was 2% (it was 99% at the initiation time and 97% after the test). White color in appearance was maintained.

A molded cylindrical product was prepared at a compression pressure of 0.5 kN in the same manner as in Example 1 and the hardness and disintegration time were measured. As a result, the hardness and the disintegration time of the molded cylindrical product were 40 N and 3600 seconds, respectively.

TABLE 1

$^1H^-$ and $^{13}C$-NMR chemical shift of a transglucosylated product in Example 1

| The number of carbon atom | σH (ppm) | J (H, H) (Hz) | σc (ppm) |
|---|---|---|---|
| 1 | 3.66 | s | 64.1 |
| 2 |  |  | 106.5 |
| 3 | 4.20 | d, 8.9 | 79.2 |
| 4 | 4.02 | dd, 8.9, 8.6 | 76.8 |
| 5 | 3.87 |  | 84.2 |
| 6 | 3.79 |  | 65.1 |
| 1' | 5.39 | d, 3.7 | 94.7 |
| 2' | 3.59 | dd, 10, 3.7 | 73.6 |
| 3' | 3.86 |  | 73.9 |
| 4' | 3.69 |  | 81.0 |
| 5' | 3.96 |  | 73.9 |
| 6' | 3.90 |  | 62.2 |

TABLE 1-continued $^1H^-$ and $^{13}C$-NMR chemical shift of a transglucosylated product in Example 1

| The number of carbon atom | σH (ppm) | J (H, H) (Hz) | σc (ppm) |
|---|---|---|---|
|  | 3.83 |  |  |
| 1" | 4.51 | d, 8.1 | 105.1 |
| 2" | 3.35 |  | 75.8 |
| 3" | 3.64 |  | 76.9 |
| 4" | 3.65 |  | 81.2 |
| 5" | 3.61 |  | 77.6 |
| 6" | 3.97 |  | 62.7 |
|  | 3.81 |  |  |
| 1''' | 4.49 | d, 8.1 | 105.4 |
| 2''' | 3.30 |  | 76.0 |
| 3''' | 3.49 |  | 78.3 |
| 4''' | 3.40 |  | 72.3 |
| 5''' | 3.47 |  | 78.8 |
| 6''' | 3.90 |  | 63.4 |
|  | 3.70 |  |  |

Chemical shift (ppm) is represented by a relative value when sodium [2,2,3,3-D4]-3-(trimethylsilyl) propanoate in heavy water is regarded as 0 ppm s: singlet d: doublet dd: double doublet

INDUSTRIAL APPLICABILITY

The present invention can provide a stable composition for applications such as medicines, agricultural chemicals, fertilizers, feed products, food products, industrial products, and cosmetic products since the present invention rarely causes the chemical interaction (such as Maillard reaction) with an active ingredient having a terminal amino group. In particular, the present invention can be suitably used in the fields of medicines, food products or the like.

The invention claimed is:

1. A β-glucan derivative having a β-glucan residue of three or more glucose residues and a fructosyl group chemically bound to a reducing end of the β-glucan residue.

2. The β-glucan derivative according to claim 1 having 3 to 1000 glucose residues.

3. The β-glucan derivative according to claim 1 having 3 to 450 glucose residues.

4. The β-glucan derivative according to claim 1 having 40 to 450 glucose residues.

5. The β-glucan derivative according to claim 1 having 3 to 39 glucose residues.

6. The β-glucan derivative according to claim 1 having 40 to 450 glucose residues, characterized in that the β-glucan derivative is used as an additive for pharmaceuticals and foods.

7. The β-glucan derivative according to claim 1 having 3 to 39 glucose residues, characterized in that the β-glucan derivative is used as an additive for pharmaceuticals and foods.

8. The β-glucan derivative according to claim 1, wherein a chemical bond between the β-glucan residue and the fructosyl group is an ether bond.

9. The β-glucan derivative according to claim 1, wherein the β-glucan derivative is powder at ordinary temperature and pressure.

10. A pharmaceutical or food composition comprising the β-glucan derivative according to claim 1 and at least one active ingredient.

11. A process for producing the β-glucan derivative according to claim 1 comprising providing a β-glucan and sucrose as substrates and allowing β-fructofuranosidase to transglucosylate a fructosyl group in said sucrose to said β-glucan.

12. A process for producing a β-glucan derivative, comprising:
    providing a β-glucan residue having three or more glucose residues and having a hydroxyl group at a C-1 position of a reducing end of the β-glucan residue; and
    transglucosylating a C-2 position of a fructosyl group to the C-1 position of the reducing end of the β-glucan residue using fructofuranosidase.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Arthrobacter globiformis NBRC 3062

<400> SEQUENCE: 1

Ala Thr Asp Ala Ala Pro Gly Phe Pro Gln
1               5                   10